United States Patent [19]

Hofmeister et al.

[11] Patent Number: 4,719,054
[45] Date of Patent: Jan. 12, 1988

[54] PROCESS FOR THE PRODUCTION OF 17α-ETHYNYL-17β-HYDROXY-18-METHYL-4,15-ESTRADIEN-3-ONE, AND NOVEL 3,5-ESTRADIEN-17-ONE STARTING COMPOUNDS FOR THIS PROCESS

[75] Inventors: Helmut Hofmeister; Henry Laurent; Hans-Peter Lorenz; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 861,775

[22] Filed: May 9, 1986

[30] Foreign Application Priority Data

May 10, 1985 [DE] Fed. Rep. of Germany ....... 3517466

[51] Int. Cl.$^4$ ................................. C07J 1/00
[52] U.S. Cl. ................................. 260/397.4
[58] Field of Search ....................... 260/397.4

[56] References Cited

U.S. PATENT DOCUMENTS 3,214,448 10/1965 Holmlund et al. ............ 260/397.45
4,036,695 7/1977 Petzoldt et al. ................ 260/397.3
4,081,537 3/1978 Hofmeister et al. ........... 260/397.45

FOREIGN PATENT DOCUMENTS 2546062 4/1977 Fed. Rep. of Germany.
2749104 5/1979 Fed. Rep. of Germany.

OTHER PUBLICATIONS

W. H. F. Schneider et al, The Efficacy of Gestoden as Ovulation Inhibitor, Weiner Klimisch Wochenschift, Oct. 16, 1981, pp. 601–604.
Donald K. Phillips et al., Estra-1,3,5(10), 15-tetraenes, J. Med. Chem. 11 (1968) pp. 924–928.
Alberto Ercoli et al., An Improved Method of Preparing Testosterone, Dihydrotestosterone and Some of their Esters, J. Am. Chem. Soc. 75 (1953).

Primary Examiner—Leonard Schenkman
Assistant Examiner—Joseph A. Lipovsky
Attorney, Agent, or Firm—Millen & White

[57] ABSTRACT

A process and novel starting materials for the production of 17α-ethynyl-17β-hydroxy-18-methyl-4,15-estradien-3-one of Formula I

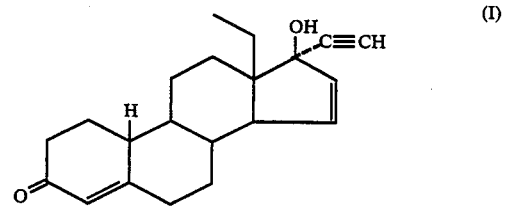

are disclosed. Novel 17-ketone starting materials have the Formula II

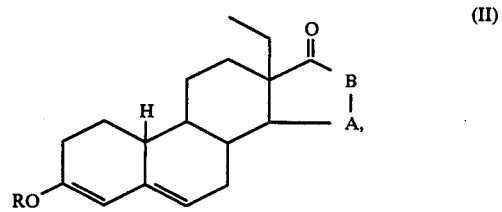

wherein
R is an alkyl residue of 1–3 carbon atoms and

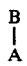

is the grouping

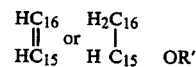

wherein R' is an acyl group of up to 10 carbon atoms.

19 Claims, No Drawings

PROCESS FOR THE PRODUCTION OF 17α-ETHYNYL-17β-HYDROXY-18-METHYL-4,15-ESTRADIEN-3-ONE, AND NOVEL 3,5-ESTRADIEN-17-ONE STARTING COMPOUNDS FOR THIS PROCESS

BACKGROUND OF THE INVENTION

Gestodene (17α-ethynyl-17β-hydroxy-18-methyl-4,15-estradien-3-one) of formula I

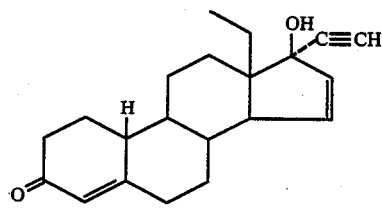

is a highly efficacious gestagen usable, for example, in contraceptive preparations; as is well known in the art and disclosed in "Wiener klinische Wochenschrift" 93 (1981) 601–604 which disclosure is incorporated by reference herein.

Several methods for the preparation of gestodene are known. In each case, the compound is produced by ethynylation of a 17-ketone.

German Pat. No. 2,546,062 discloses ethynylations on 17-ketones of the following general Formula III:

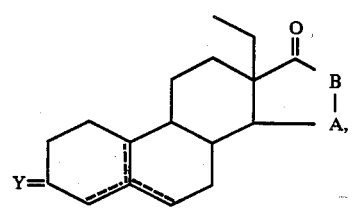

wherein Y is a free keto group or preferably a keto group blocked as a ketal, and one of the ==== bonds in the 4,5-, 5,6- or 5,10-position means a carbon-carbon double bond and the other bonds mean respectively one carbon-carbon single bond, and A-B means a carbon-carbon double bond or the grouping

wherein R' represents a hydrogen atom, a silyl, acyl, sulfonyl or nitro group.

By treating 18-methyl-4,15-estradiene-3,17-dione (Formula III: Y=O, A-B=CH=CH) with lithium acetylide, gestodene is obtained in a high yield of about 75%. However, this method is usable only for amounts of starting material compounds up to 100 g; ethynylation in this manner therefore cannot be performed on an industrial scale. Moreover, it has been found that the 18-methyl-4,15-estradiene-3,17-dione starting material can have a sensitizing effect in case of skin contact, consequently protective measures must be observed when handling 18-methyl-4,15-estradiene-3,17-dione.

Preparation of gestodene by way of the 3-ketals (Formula III: Y=ethylenedioxy or 2,2-dimethyl-1,3-propylenedioxy) has the drawback that the 3-ketals are obtained as mixtures of isomers in an oily form which can be purified only by chromatography.

German Pat. No. 2,749,104 which disclosure is incorporated by reference herein describes ethynylation on 17-ketones wherein the 3-keto group is blocked with 1,2-ethanedithiol (Formula III: Y=ethylene-dithio with a carbon-carbon double bond in the 4,5-position). Ethanedithiol constitutes a pollutant, even in small amounts, on account of its unpleasant odor. Furthermore, use of the thioketal blocking group is disadvantageous in that it can be split off after ethynylation only with a large excess of methyl iodide, an expensive reagent. Thus, any advantages of the thioketals such as ready crystallizability and almost quantitative conversion capability are outweighed.

SUMMARY OF THE INVENTION

It is therefore an object of the invention to avoid the drawbacks of the conventional methods by providing an improved production process for gestodene. It is a further object to provide novel starting material for said process.

Upon further study of the specification and appended claims, further objects and advantages of this invention will become apparent to those skilled in the art.

These objects have been achieved by the provision of novel 17-ketones of general Formula II

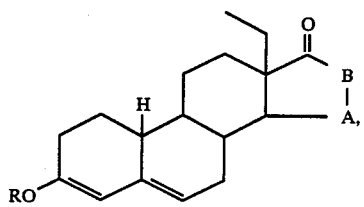

wherein R stands for an alkyl residue of 1-3 carbon atoms and

stands for the grouping

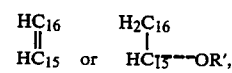

wherein R' is an acyl group containing up to 10 carbon atoms, said compounds being readily crystallizable and especially well suited for the preparation of gestodene. Ethynylation (e.g., with lithium acetylide), with splitting off of HOR' to form the 15,16-double bond, and 3-dienol ether cleavage to obtain gestodene can be performed in a one pot process in high yields.

Accordingly, the invention provides a novel process for the production of gestodene by ethynylation of novel compounds of general Formula II.

DETAILED DISCUSSION

In Formula II, R stands for an alkyl residue of 1-3 carbon atoms, the methyl and ethyl residues being preferred. Suitable acyl residues R' are the residues of organic carboxylic acids of up to 10 carbon atoms, usually hydrocarbon based; preferably acetyl, trifluoroacetyl, trimethylacetyl, propionyl, butyryl, heptanoyl and benzoyl residues. All are equivalents for this invention as are similar groups.

Ethynylation of the 17-ketone of general Formula II takes place with lithium acetylide under conditions employed in conjunction with other different reactions, e.g., as disclosed in J. Med. Chem. 11 (1968) 924–928. which disclosure is incorporated by reference herein. Lithium acetylide can also be formed in situ and made to react with the 17-ketone of Formula II. Thus, the 17-ketone can be treated, for example, in a suitable solvent such as tetrahydrofuran, with a solution of alkyllithium and acetylene in tetrahydrofuran and hexane, or in tetrahydrofuran and diethyl ether, at temperatures of between $-70°$ C. and room temperature. Alkyllithium is preferably utilized as n-butyllithium in a 15% strength solution of hexane or as methyllithium in etheral solution. Lithium acetylide in tetrahydrofuran is prepared in situ, e.g., by addition of acetylene to a cold solution of n-butyllithium (15% in hexane) in tetrahydrofuran or by addition of n-butyllithium solution to ice-cold tetrahydrofuran saturated with acetylene. Besides tetrahydrofuran other ethers like dioxan and methyl-tert.butyl ether are preferred for use with n-butyllithium.

The group OR', when contained in the 17-ketone, is split off under ethynylation as HOR' to form the 15,16-double bond. Subsequent cleavage of the 3-dienol ether group to the 3-keto group is also conducted according to methods known to persons skilled in the art in conjunction with other different reactions, and detailed in J. Am. Chem. Soc. 75 (1953) 650–653. Usable reagents for dienol ether cleavage, for example, are mineral acids, such as, for instance perchloric acid, sulfuric acid or hydrochloric acid, or organic acids, such as, for example, oxalic acid. Cleavage is preferably performed in alcoholic solution at temperatures of between about 20° and 100° C., and at a pH of 1–5.

The novel 17-ketones of general Formula II may be produced from 15α-hydroxy-18-methyl-4-estrene-3,17-dione which is described in German Pat. No. 2,546,062, which disclosure is incorporated by reference herein. Production of the ketones may be either by splitting off water from the 15,16-position and conversion into the 3-dienol ether, or by acylation of the 15α-hydroxy group and conversion into the 3-dienol ether.

Splitting off water to obtain the 15,16-double bond takes place in a manner known per se with methanesulfonyl chloride in pyridine by way of the 15α-mesylate and further treatment of the mesylate with dimethylformamide and anhydrous sodium acetate, as disclosed in U.S. Pat. No. 4,036,695 which disclosure is incorporated by reference herein.

The acylation of the 15α-hydroxy group takes place conventially as disclosed in U.S. Pat. No. 3,214,448 which disclosure is incorporated by reference herein. For example, the ketone can be reacted with a corresponding carboxylic acid anhydride or chloride (e.g., wherein R'=an acyl group of up to 10 carbon atoms) in the presence of a tertiary amine. Especially suitable as tertiary amines are pyridine and dimethylaminopyridine or mixtures of pyridine and dimethylaminopyridine.

Selective conversion of the 3,17-diketone into the 3-dienol ether maybe accomplished with trialkyl orthoformate in dioxane or with 2,2-dialkoxypropane in dimethylformamide, in tetrahydrofuran or in dioxane in the presence of an acid, such as p-toluenesulfonic acid or pyridinium tosylate. Such a conversion is conventional and is disclosed in J. Am. Chem. Soc. 75 (1953) 650–653 which disclosure is incorporated by reference herein.

In the preparation of gestodene by ethynylation and enol cleavage, preferred reaction time is 0.5–2.0 hours. Preferred relative amounts of lithium acetylide are about 3–7 mols, preferred relative amounts of alkyllithium are about 3–7 mols, preferred relative amounts of mineral acid are about 6–9 mols, preferred relative amounts of organic acid are about 4–7 mols, all based on initial amounts of the 17-ketone employed.

In the preparation of the 17-ketone, preferred relative amounts of methanesulfonylchloride are 1.1–2 mols, preferred relative amounts of pyridine are 2.5–5 ml/g, preferred relative amounts of dimethylformamide are 1.0–4 ml/g, preferred relative amounts of sodium acetate are 2–4 mols, preferred relative amounts of carboxylic anhydride/chloride are 5–7 mols, preferred relative amounts of tertiary amine are 3–5 ml/g, preferred relative amounts of trialkyl orthoformate are 5–12 mols, preferred relative amounts of dioxane are 4–8 ml/g, preferred relative amounts of 2,2-dialkoxypropane are 20–30 mols, preferred relative amounts of dimethylformamide are 7–9 ml/g, all based on initial amounts of 15-hydroxy-18-methyl-4-estrene-3,17-dione employed. Preferred reaction temperatures for the reaction with methanesulfonyl chloride are $-10°-+10°$ C., preferred reaction times are 15–25 hours.

Preferred reaction temperatures for the acylation reaction are $-10°-+30°$ C., preferred reaction times are 0.5–2 hours.

The novel 3-dienol ethers are obtained in an almost quantitative yield as a uniform product. In spite of their ready cleavability, the crystalline dienol ethers are stable and storable. Consequently, they are especially well suited for the further reaction to gestodene by ethynylation and enol ether cleavage.

The preparation of novel 17-ketones of general Formula II will be described in greater detail with reference to the examples set forth below.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

PREPARATION OF THE NOVEL STARTING MATERIALS

Direction I (a) 18-Methyl-4,15-estradiene-3,17-dione

At 0° C., 77.5 ml of methanesulfonyl chloride is added dropwise within 10 minutes to 250 g of 15α-hydroxy-18-methyl-4-estrene-3,17-dione in 704 ml of pyridine. After 3.5 hours, 350 ml of dimethylformamide and 283 g of anhydrous sodium acetate are added, the mixture is stirred under argon for 20 hours at room temperature, and the reaction mixture is introduced into ice water. The thus-precipitated product is suctioned off, washed with water, and dried under vacuum. For purposes of purification, the crude product (212 g) is treated with 21 g of active carbon in 1,500 ml of ethyl acetate and 0.4 ml of pyridine. After concentrating the solution to 420 ml, 188 g of 18-methyl-4,15-estradiene-3,17-dione is crystallized at 0° C. Melting point 156.9° C. (from acetone/hexane).

(b) 3-Methoxy-18-methyl-3,5,15-estratrien-17-one

Under argon, 20.0 g of 18-methyl-4,15-estradiene-3,17-dione in 100 ml of 1,4-dioxane and 100 ml of trimethyl orthoformate is agitated with 800 mg of p-toluenesulfonic acid at 50° C. After 2.5 hours, 10 ml of pyridine is added and the solution extensively distilled under vacuum. The residue is dissolved in ethyl acetate, washed with water, and dried. Chromatography of the crude product with 0-20% ethyl acetate-hexane yields 14.0 g of 3-methoxy-18-methyl-3,5,15-estratrien-17-one, melting point 162.1° C. (from methanol).

Direction II (a) 15α-Acetoxy-18-methyl-4-estrene-3,17-dione 200 ml of acetic anhydride is added dropwise to 100 g of 15α-hydroxy-18-methyl-4-estrene-3,17-dione in 350 ml of pyridine. After one hour, the reaction mixture is stirred into ice water. The thus-precipitated product is suctioned off, washed neutral with water, and dried under vacuum at 50° C., thus obtaining 100 g of 15α-acetoxy-18-methyl-4-estrene-3,17-dione. A sample recrystallized from acetone/hexane melts at 165° C.

(b) 15α-Acetoxy-3-methoxy-18-methyl-3,5-estradien-17-one 60.0 g of 15α-acetoxy-18-methyl-4-estrene-3,17-dione in 500 ml of dimethylformamide is stirred with 500 ml of 2,2-dimethoxypropane, 20 ml of methanol and 6.0 g of pyridinium tosylate at 110° C. under argon. After 3.5 hours, 9.0 g of solid sodium bicarbonate is added, the reaction mixture is stirred into 10 liters of ice/water, the precipitated product is suctioned off, washed repeatedly with water, and dried under vacuum at 70° C. The crude product is suspended in 375 ml of methanol and stirred under reflux for 15 minutes. After gradual cooling down to room temperature, the colorless crystallized product is suctioned off and washed with cold methanol. Yield: 56 g of 15α-acetoxy-3-methoxy-18-methyl-3,5-estradien-17-one. Melting point 190° C.

Direction III

15α-Acetoxy-3-ethoxy-18-methyl-3,5-estradien-17-one

Under argon, 2.0 g of 15α-acetoxy-18-methyl-4-estrene-3,17-dione in 60 ml of dioxane is agitated at room temperature for 20 hours with 6 ml of triethyl orthoformate and 40 mg of p-toluenesulfonic acid. After adding 2 ml of pyridine, the mixture is diluted with ether, washed with water, and dried. The crude product is recrystallized from acetone/hexane. Yield: 1.6 g of 15α-acetoxy-3-ethoxy-18-methyl-3,5-estradien-17-one. Melting point: 202° C.

Direction IV (a) 15α-Benzoyloxy-18-methyl-4-estrene-3,17-dione

At 0° C., 5 ml of benzoyl chloride is added dropwise to 5 g of 15α-hydroxy-18-methyl-4-estrene-3,17-dione in 20 ml of pyridine. After 45 minutes, 2 ml of water is added, the mixture is stirred for another 30 minutes, and then the reaction mixture is poured into ice/water. The thus-precipitated product is suctioned off, dissolved in methylene chloride, washed with water, and dried over sodium sulfate. After chromatography of the crude product on silica gel with an acetone-hexane gradient, 5.6 g of 15α-benzoyloxy-18-methyl-4-estrene-3,17-dione is obtained as a foam.

(b) 15α-Benzoyloxy-3-methoxy-18-methyl-3,5-estradien-17-one

Analogously to Direction II(b), 7.8 g of 15α-benzoyloxy-18-methyl-4-estrene-3,17-dione is reacted with dimethoxypropane and worked up, thus obtaining 6.8 g of 15α-benzoyloxy-3-methoxy-18-methyl-3,5-estradien-17-one as a foam.

Direction V (a) 18-Methyl-15α-trimethylacetoxy-4-estrene-3,17-dione 10 g of 15α-hydroxy-18-methyl-4-estrene-3,17-dione in 200 ml of pyridine is combined with 2 g of dimethylaminopyridine and 20 ml of pivalic anhydride and agitated for one hour at 50° C. The mixture is introduced into ice/water, extracted with ethyl acetate, washed neutral with water, and dried over sodium sulfate. Chromatography of the crude product on silica gel with an acetone-hexane gradient yields 9.5 g of 18-methyl-15α-trimethylacetoxy-4-estrene-3,17-dione as a foam.

(b) 3-Methoxy-18-methyl-15α-trimethylacetoxy-3,5-estradien-17-one

In analogy to Direction II(b), 5.6 g of 18-methyl-15α-trimethylacetoxy-4-estrene-3,17-dione is reacted with dimethoxypropane and worked up, thus obtaining 4.9 g of 3-methoxy-18-methyl-15α-trimethylacetoxy-3,5-estradien-17-one.

EXAMPLE 1

17α-Ethynyl-17β-hydroxy-18-methyl-4,15-estradien-3-one (a) From 3-Methoxy-18-methyl-3,5,15-estratrien-17-one At 0° C., acetylene is introduced for 15 minutes into a solution of 40 ml of n-butyllithium (15% in hexane) in 100 ml of absolute tetrahydrofuran and then 4.0 g of 3-methoxy-18-methyl-3,5,15-estratrien-17-one in 40 ml of tetrahydrofuran is added dropwise thereto. After 15 minutes, the mixture is combined with 8 ml of water, 40 ml of methanol and 8 g of oxalic acid, stirred for one hour at 60° C., 600 ml of water is added, and the mixture is extracted with ethyl acetate. The organic phase is washed with water and dried. Recrystallization from ethyl acetate yields 2.4 g of 17α-ethynyl-17β-hydroxy-18-methyl-4,15-estradien-3-one. Melting point 197° C.

(b) From 15α-Acetoxy-3-methoxy-18-methyl-3,5-estradien-17-one

Acetylene is introduced for 15 minutes into a solution of 50 ml of n-butyllithium (15% in hexane) in 130 ml of absolute tetrahydrofuran. The resultant lithium acetylide solution is added dropwise at 0° C. under argon to 5.0 g of 15α-acetoxy-3-methoxy-18-methyl-3,5-estradien-17-one in 50 ml of tetrahydrofuran. After all of the lithium acetylide solution has been added, the mixture is stirred for 15 minutes, then gently combined with 20 ml of 50% hydrochloric acid, stirred for another 30 minutes and thereafter diluted with ethyl acetate. The organic phase is repeatedly washed with water, dried over sodium sulfate, and concentrated under vacuum. The crude product is treated in acetone with active carbon and recrystallized from acetone/hexane. Yield: 3.7 g of 17α-ethynyl-17β-hydroxy-18-methyl-4,15-estradien-3-one, melting point 197.8° C.

(c) From 15α-Benzoyloxy-3-methoxy-18-methyl-3,5-estradien-17-one

As described in 1(b), 3.6 g of 15α-benzoyloxy-3-methoxy-18-methyl-3,5-estradien-17-one is reacted with lithium acetylide. After completed reaction, the reaction mixture is combined with saturated ammonium chloride solution, diluted with ethyl acetate, washed with water, and dried over sodium sulfate. The resultant 17α-ethynyl-3-methoxy-18-methyl-3,5,15-estratrien-17β-ol is stirred, in the form of the crude product, in 70 ml of methanol and 6 ml of water with 3 g of oxalic acid for 10 minutes under reflux. The reaction mixture is introduced into ice/water. The thus-precipitated product is suctioned off, dissolved in ethyl acetate, washed with water, and dried over sodium sulfate. Recrystallization from acetone/hexane yields 1.9 g of 17α-ethynyl-17β-hydroxy-18-methyl-4,15-estradien-3-one, melting point 197.8° C.

(d) From 3-Methoxy-18-methyl-15α-trimethylacetoxy-3,5-estradien-17-one

Analogously to Example 1(b), 2.8 g of 3-methoxy-18-methyl-15α-trimethylacetoxy-3,5-estradien-17-one is reacted with lithium acetylide and worked up. Recrystallization from acetone/hexane yields 1.6 g of 17α-ethynyl-17β-hydroxy-18-methyl-4,15-estradien-3-one, melting point 197° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

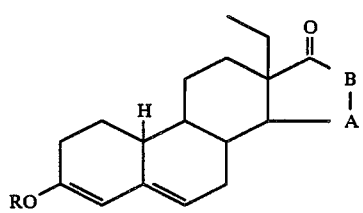

wherein R is C$_{1-3}$-alkyl, $$\begin{array}{c} B \\ | \\ A \end{array}$$

is the grouping

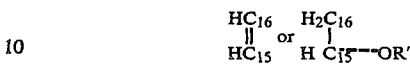

wherein R' is a C$_{1-10}$-acyl group of a hydrocarbon carboxylic acid.

2. A compound of claim 1, wherein R is methyl or ethyl.

3. A compound according to claim 1, wherein

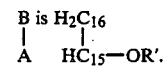

4. A compound according to claim 1, wherein R' is acetyl.

5. A compound according to claim 1, wherein R' is benzoyl.

6. 3-Methoxy-18-methyl-3,5,15-estratrien-17-one, a compound of claim 1.

7. 15α-Acetoxy-3-methoxy-18-methyl-3,5-estradien-17-one, a compound of claim 1.

8. 15α-Acetoxy-3-ethoxy-18-methyl-3,5-estradien-17-one, a compound of claim 1.

9. 15α-Benzoyloxy-3-methoxy-18-methyl-3,5-estradien-17-one, a compound of claim 1.

10. 3-Methoxy-18-methyl-15α-trimethyl-acetoxy-3,5-estradien-17-one, a compound of claim 1.

11. A process for the production of 17α-ethynyl-17-βhydroxy-18-methyl-4,15-estradien-3-one, comprising ethynylating a compound of claim 1 with lithium acetylide, and treating resultant product with an acid.

12. A process of claim 11 wherein said acid treatment step is carried out in situ.

13. A process according to claim 11, wherein the lithium acetylide is formed in situ from an alkyllithium compound and acetylene.

14. A process according to claim 13, wherein the alkyllithium compound is n-butyllithium.

15. A process according to claim 13, wherein the acid is a mineral acid.

16. A process according to claim 13, wherein the acid is perchloric acid, sulfuric acid, or hydrochloric acid.

17. A process according to claim 13, wherein the acid is oxalic acid.

18. A process according to claim 13, wherein the reaction is performed in a solution of tetrahydrofuran and hexane.

19. A process according to claim 13, wherein the reaction is performed in a solution of tetrahydrofuran and diethyl ether.

* * * * *